United States Patent
Mewshaw et al.

(10) Patent No.: US 6,221,863 B1
(45) Date of Patent: Apr. 24, 2001

(54) 3,4-DIHYDRO-2H-BENZO[1,4]OXAZINE DERIVATIVES

(75) Inventors: Richard E. Mewshaw, King of Prussia, PA (US); Uresh S. Shah, Cranbury, NJ (US)

(73) Assignee: American Home Products Corp., Madison, NJ (US)

( * ) Notice: Subject to any disclaimer, the term of this patent is extended or adjusted under 35 U.S.C. 154(b) by 0 days.

(21) Appl. No.: 09/475,383

(22) Filed: Dec. 30, 1999

Related U.S. Application Data

(60) Provisional application No. 60/126,411, filed on Jan. 7, 1999, now abandoned.

(51) Int. Cl.⁷ .................. A61K 31/538; C07D 413/14
(52) U.S. Cl. ........................... 514/230.5; 544/105
(58) Field of Search ................. 544/105; 514/230.5

(56) References Cited

U.S. PATENT DOCUMENTS

| 3,058,980 | 10/1962 | Berg et al. ............ 260/244 |
| 4,612,312 | 9/1986 | Hibert et al. ........... 514/255 |

FOREIGN PATENT DOCUMENTS

| 8907596 | 8/1989 | (WO) . |
| WO99/51592 | 10/1999 | (WO) . |

OTHER PUBLICATIONS

Le Puol et al., *Arch. Pharmacol*, 352:141 (1995).
Artigas et al., *Trends Neurosci.*, 19:378–383 (1996).
Bourlot, Anne–Sophie, et al., *New Substituted, 1,4–Benzosazine Derivatives with Potential Intracellular Calcium Activity* J. Med. Chem 1998, 41. pp. 3142–3158.

*Primary Examiner*—Richard L. Raymond
(74) *Attorney, Agent, or Firm*—Michael R. Nagy

(57) ABSTRACT

Compounds are provided having the following formula:

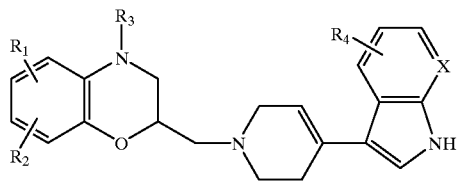

wherein:
- $R_1$ is hydrogen or halogen;
- $R_2$ is hydrogen, alkoxy or carboximide;
- $R_3$ is hydrogen, alkyl, alkylaryl, aryl or substituted aryl;
- $R_4$ is hydrogen, CN, halogen, or carboximide; and
- X is CH or N; or pharmaceutically acceptable salts thereof.

11 Claims, No Drawings

3,4-DIHYDRO-2H-BENZO[1,4]OXAZINE DERIVATIVES

CROSS REFERENCE TO RELATED APPLICATIONS

This application claims the benefit of U.S. Provisional Application No. 60/126,411, filed Jan. 7, 1999.

FIELD OF THE INVENTION

This invention is directed to compounds useful in the treatment of neurological disease caused by disorders of the serotonin-affected neurological systems, such as depression and anxiety. More specifically, the present invention is directed to 3,4-Dihydro-2H-benzo[1,4]oxazine derivatives useful as anxiolytic and/or antidepressant agents.

BACKGROUND OF THE INVENTION

Compounds which enhance the neurotransmission of serotonin (5-HT) are known to be useful for the treatment of many psychiatric disorders, including depression and anxiety. The first generation of non-selective serotonin-affecting drugs operated through a variety of physiological means which caused them to possess numerous undesired side effects. The more currently prescribed drugs, the selective serotonin reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of 5-HT neurons, causing a dampening of the therapeutic effect. Studies suggest that after several weeks of SSRI administration, a desensitization of the 5-HT autoreceptors occurs allowing a full antidepressant effect in most patients (see e.g., LePoul et al., *Arch. Pharmacol.*, 352:141 (1995)). Hence, it is believed that overriding this negative feedback by using 5HT1A antagonists would potentially increase and accelerate the clinical antidepressant response. Recent studies by Artigas et al., *Trends Neurosci.*, 19:378–383 (1996) suggest a combination of 5-HT1A activity and inhibition of 5-HT uptake within a single molecular entity can achieve a more robust and fast-acting antidepressant effect.

U.S. Pat. No. 3,058,980 discloses the preparation of compounds of the following formula which are known to exhibit analgesic activity.

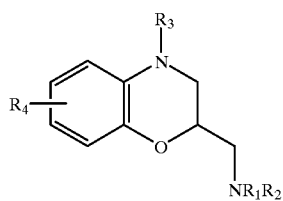

WO 8907596-A discloses the preparation of compounds having the following formula which are active in a variety of CNS disorders, including depression and schizophrenia.

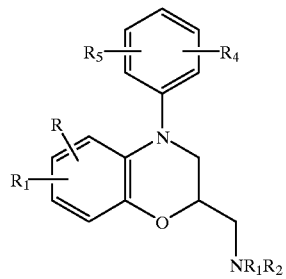

U.S. Pat. No. 4,612,312 discloses compounds of the following formula as anxiolytic and antihypertensive agents.

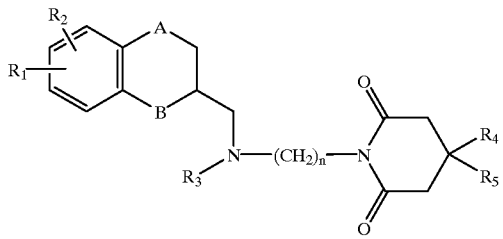

SUMMARY OF THE INVENTION

The present invention relates to a new class of molecules which have the ability to act at the 5-HT1A autoreceptors and concommnitantly with the 5-HT transporter. Such compounds are therefore potentially useful for the treatment of depression as well as other serotonin disorders.

The compounds of this invention are 3,4-dihydro-2H-benzo[1,4]oxazine derivatives represented by Formula I:

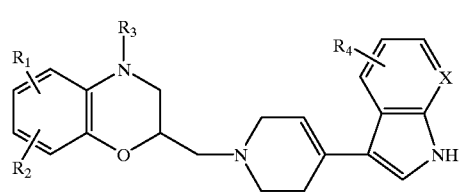

I wherein:
$R_1$ is hydrogen or halogen;
$R_2$ is hydrogen, alkoxy or carboximide;
$R_3$ is hydrogen, alkyl, alkylaryl, aryl or substituted aryl;
$R_4$ is hydrogen, CN, halogen or carboximide; and
X is CH or N; or pharmaceutically acceptable salts thereof.

DETAILED DESCRIPTION OF THE INVENTION

Preferably, the compounds of the present invention are those of Formula I, wherein
$R_1$ is hydrogen;
$R_2$ is alkoxy or hydrogen;
$R_3$ is hydrogen, alkyl or alkylaryl;
$R_4$ is halogen or hydrogen; and
X is CH or N; or pharmaceutically acceptable salts thereof.

More preferably, the compounds of the present invention are:

2-[4-(5-Fluoro-1H-indol-3-yl)-3,6-dihydro-2H-pyridin-1-ylmethyl]-8-methoxy-3,4-dihydro-2H-benzo[1,4]oxazine;

2-[4-(5-Fluoro-1H-indol-3-yl)-3,6-dihydro-2H-pyridin-1-ylmethyl]-8-methoxy4-methyl-3,4-dihydro-2H-benzo[1,4]oxazine;

2-[4-(5-Fluoro-1H-indol-3-yl)-3,6-dihydro-2H-pyridin-1-ylmethyl]-[-methoxy-4-ethyl-3,4-dihydro-2H-benzo[1,4]oxazine;

2-[4-(5-Fluoro-1H-indol-3-yl)-3,6-dihydro-2H-pyridin-1-ylmethyl]-8-methoxy-4-propyl-3,4-dihydro-2H-benzo[1,4]oxazine;

2-[4-(1H-Indol-3-yl)-3,6-dihydro-2H-pyridin-1-ylmethyl]-3,4-dihydro-2H-benzo[1,4]oxazine;

4-Phenyl-2-[4-(1H-pyrrolo[2,3,b]pyridin-3-yl)-3,6-dihydro-2H-pyridin-1-ylmethyl]-3,4-dihydro-2H-benzo[1,4]oxazine; and 2-[4-(5-Fluoro-1H-indol-3-yl)-3,6-dihydro-2H-pyridin-1-ylmethyl]-8-methoxy-4-(4-trifluoromethyl-phenyl)-3,4-dihydro-2H-benzo[1,4]oxazine.

As used herein, the terms "alkyl" and "alkoxy" are meant to include both straight and branched carbon chains containing 1–6 carbon atoms. The term "aryl" is meant to include aromatic radicals of 6–12 carbon atoms. The term "halogen" is meant to include fluorine, chlorine, bromine, and iodine.

The compounds of this Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric, hydrobromic, sulfuric, cyclohexylsulfamic, phosphoric and nitric acids.

The compounds of the present invention may be prepared by any suitable method which will be recognized by those skilled in the art. However, the present compounds may be advantageously prepared according to Schemes 1–5 set forth below.

Scheme 1

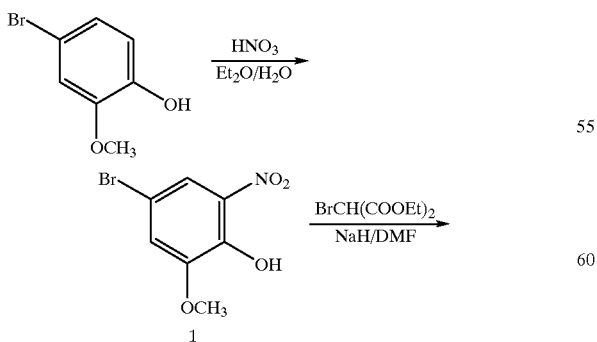

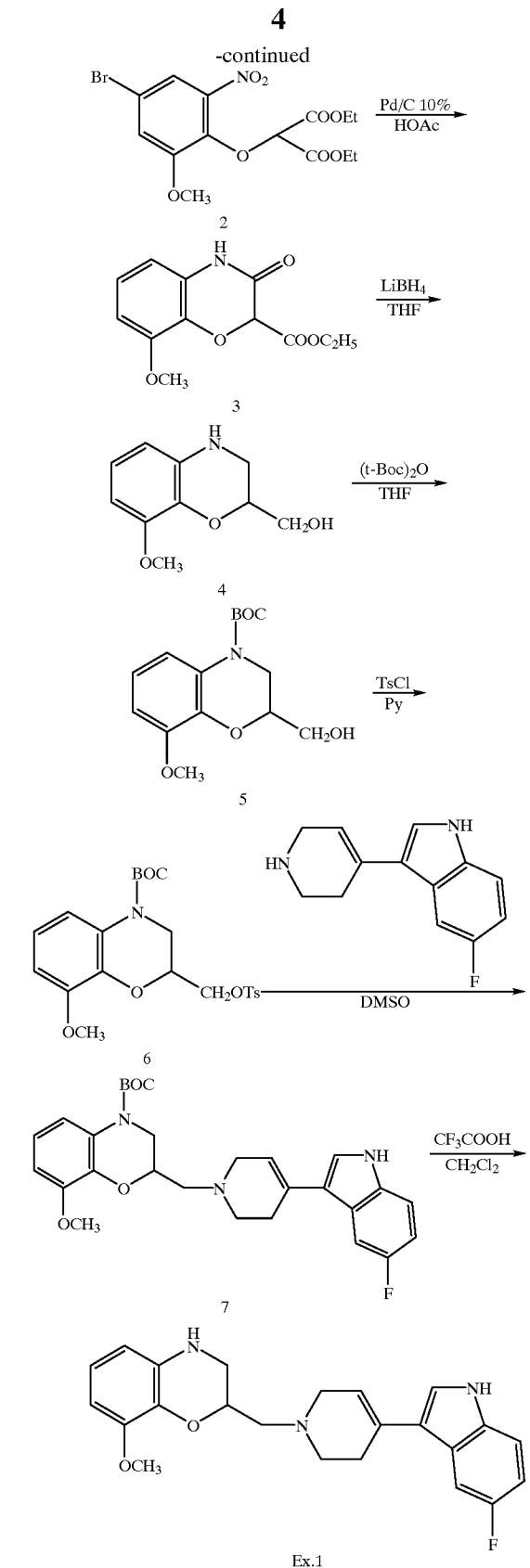

Ex.1

Scheme 2
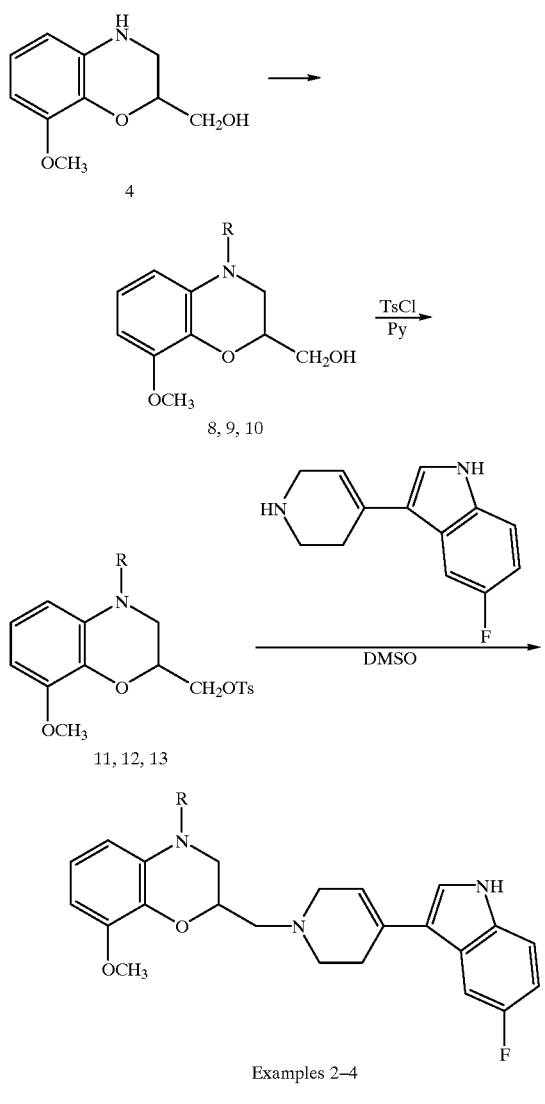
Examples 2–4
Scheme 3
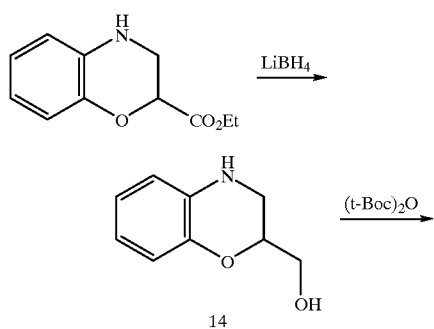
-continued
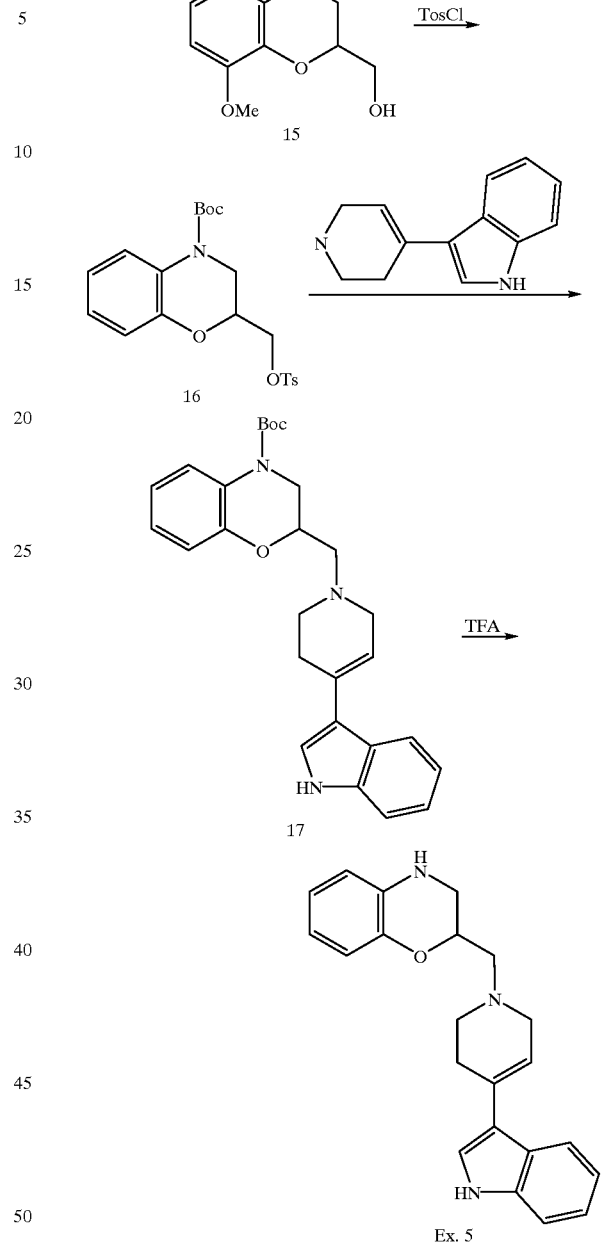
Ex. 5
Scheme 4
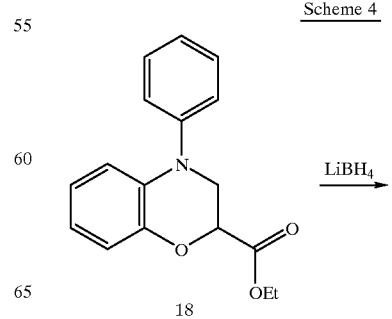

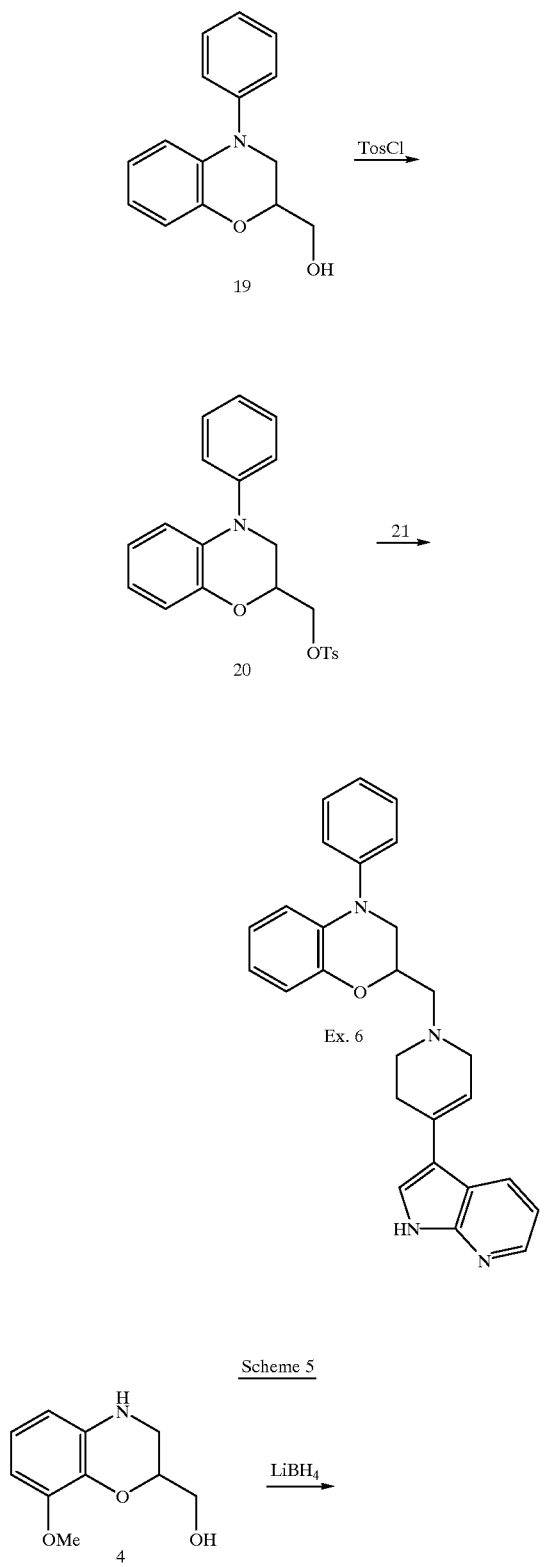
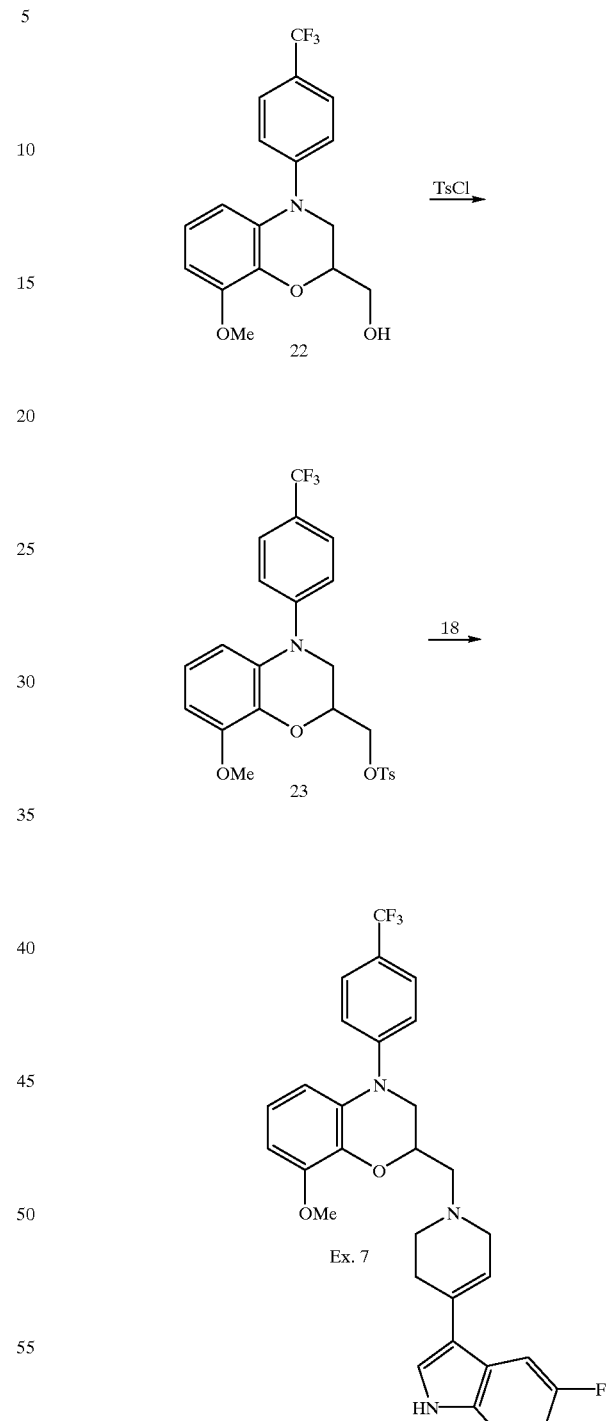
INTERMEDIATE 1
4-Bromo-6-nitroguaicol
To a two-phase, rapidly stirred solution of 4-bromoguaiacol (53.78 g, 0.26 mmol) in ethyl ether (328 ml) and water (109 ml) was added concentrate nitric acid (17 ml) over 25 minutes. The resulting solution was stirred at room temperature for 20 minutes. The ethyl ether was separated and methylene chloride was added to ethyl ether to completely dissolve the yellow crystals. The organic layer was dried over anhydrous magnesium sulfate, filtered and concentrated. Chromatography (1:4.5:1.5=ethyl acetate: hexanes: methylene chloride) afforded 32.9 g (50%) of product as a yellow solid: mp 109–110° C.; $^1$H NMR (400 MHz, CDCl$_3$): δ3.95 (3H, s), 7.19 (2H, m), 7.85 (1H, m), 10.7 (1H, s).

Elemental analysis for $C_7H_6BrNO_4$

Calc'd;: C, 33.90; H. 2.44; N. 5.65

Found: C, 33.90; H, 2.32; N, 5.38

INTERMEDIATE 2

2-(4-Bromo-2-methoxy-6-nitro-phenoxy)-malonic acid diethyl ester

A mixture of sodium hydride (0.9 g, 20 mmol) in N,N-dimethylformamide (40 ml) was stirred at room temperature and a solution of nitrophenol (5.0 g, 20 mmol) in N,N-dimethylformamide (10 ml) in was added dropwise and stirred for 45 minutes. The reaction mixture was cooled to 0° C. and diethyl bromomalonate (7 ml, 20 mmol) was slowly added to the reaction mixture. The reaction was stirred for 2 hours at ice bath temperature and allowed to warm to room temperature for 48 hours. The mixture was then poured into water and extracted with ethyl acetate, washed with 1N sodium hydroxide, water and brine. The organic layer was dried over anhydrous magnesium sulfate and filtered. The solvent was removed under vacuum. Chromatography (60% ethyl acetate-hexanes) afforded 6.4 g (78.3% ) of product as white solid: mp 59–61° C.; $^1$H NMR (400 MHz, CDCl$_3$): δ 1.30 (6H,t, J=7.04 Hz), 3.88 (3H, s), 4.29 (2H, dq, J=0.88, 7.04 Hz), 7.20 (1H, d, J=2.2 Hz), 7.50 (1H, d, J=2.2Hz).

Elemental analysis for $C_{14}H_{16}BrNO_8$

Calc'd;: C, 41.40; H, 3.97; N, 3.45

Found: C, 41.55; H, 3.76; N, 3.32

INTERMEDIATE 3

8-Methoxy-3-oxo-3,4-dihydro-2H-benzo[1,4] oxazine-2-carboxylic acid ethyl ester

A mixture of Intermediate 2 and 10% palladium on carbon (0.1 g) in acetic acid (10 ml) was hydrogenated at 35 psi for 5 hours. The catalyst was filtered and the solvent removed under vacuum. The reaction mixture was diluted with water and extracted with ethyl acetate. The organic layer was washed with water, brine and dried over anhydrous magnesium sulfate, filtered and the solvent was removed under vacuum to afford a crude solid. Recrystallization in ethyl acetate gave 0.7 g (68%) of product as a white solid: mp 173–174° C.; $^1$H NMR (400 MHz, CDCl$_3$): δ1.25 (3H, t, J=7 Hz), 3.92 (3H, s), 4.12–4.30 (m, 2H), 5.27 (1H, s), 6.48 (1H, dd, J=1.32, 7.92 Hz), 6.66 (1H, dd, J=1.32, 8.32 Hz), 6.92 (1H, t, J=8.34 Hz), 8.88 (1H, s); MS (+) ESI m/e 252 (M$^+$).

Elemental analysis for $C_{12}H_{13}NO_5.0.25H_2O$

Calc'd;: C, 56.35; H, 5.32; N, 5.47

Found: C, 56.36; H, 5.02; N, 5.38

INTERMEDIATE 4

(8-Methoxy-3,4-dihydro-2H-benzo[1,4]oxazin-2-yl)-methanol

A mixture of Intermediate 3 (2.3 g, 9.2 mmol) in tetrahydrofuran (200 ml) was stirred at room temperature and lithium borohydride (0.9 g, 42 mmol) was added to above solution in small portions. The reaction mixture was heated to 65° C. for 20 hours. The excess lithium borohydride was destroyed by the cautious addition of water. The mixture was concentrated and extracted with ethyl acetate and washed with brine. The organic layer was dried over anhydrous magnesium sulfate, filtered and concentrated to afford 1.7 g (100%) of a crude product as a white solid: mp 108–110° C. $^1$H NMR (400 MHz, CDCl$_3$) δ 3.00 (1H,m), 3.30 (1H, m), 3.48 (1H, m), 3.58 (1H, m), 3.66 (3H, s), 3.88 (1H, m), 4.87 (1H, t, J=5.72 Hz), 5.65 (1H, br), 6.19 (2H, m), 6.55 (1H, t, J=8.12 Hz).

Elemental analysis for $C_{10}H_{13}NO_8.0.15C_4H_8O$

Calc'd;: C, 60.95; H, 6.57; N, 6.88

Found: C, 61.08; H, 6.86; N, 6.71

INTERMEDIATE 5

2-Hydroxymethyl-8-methoxy-2,3-dihydro-benzo[1,4]oxazine-4-carboxylic acid tert-butyl ester A mixture of Intermediate 4 (2.5 g, 12.8 mmol) and di-t-butyl dicarbonate (9.2 g, 42 mmol) in anhydrous tetrahydrofuran (100 ml) was heated to reflux temperature for 2 hours. The reaction mixture was concentrated and chromatographed (50% ethyl acetate-hexanes) to afford 1.74 g (46% ) of product as white solid: mp 65–68° C.; $^1$H NMR (400 MHz, CDCl$_3$) δ 1.52 (9H, s), 2.28 (1H, br), 3.76–3.93 (7H, m), 4.40 (1H, m), 6.64 (1H, dd, J=1.32, 8.12Hz), 6.82 (1H, t, J=8.36 Hz), 7.26 (1H, br).

Elemental analysis for $C_{15}H_{21}NO_5$

Calc'd;: C, 61.00; H, 7.17; N, 4.74

Found: C, 60.65; H, 7.09; N, 4.70

INTERMEDIATE 6

8-Methoxy-2-(toluene-4-sulfonyloxymethyl)-2,3-dihydro-benzo[1,4]oxazine-4-carboxylic acid tert-butyl ester A mixture of Intermediate 5 (1.6 g) and p-toluenesulfonyl chloride (2.2 g) in dry pyridine (45 ml) was stirred at room temperature for 18 hours. The reaction mixture was diluted with ethyl acetate and sequentially washed with 2N hydrochloric acid, water and brine. The organic layer was dried over anhydrous magnesium sulfate, filtered and concentrated to give 1.7 g of solid which was recrystallized (10% ethyl acetate-hexanes) to afford 1.5 g (60%) of product as a white solid: mp 72–74°; $^1$H NMR (400 MHz, CDCl$_3$) δ 1.53 (9H, s), 2.44 (3H, s), 3.65 (1H, m), 3.83 (3H, s), 3.98 (1H, m), 4.12 (1H, dd, J=6.8, 10.56 Hz), 4.24 (1H, dd, J=4.6, 10.56), 4.45 (1H, m), 6.60 (1H, d, J=1.32 Hz), 6.82 (1H, t, J=8.36 Hz), 7.32 (2H, m), 7.79 (2H, m).

Elemental analysis for $C_{22}H_{27}NO_7S$

Calc'd: C, 58.78; H, 6.05; N, 3.12

Found: C, 58.45; H, 6.03; N, 3.07

INTERMEDIATE 7

2-[4(5-Fluoro-1H-indol-3-yl)-3,6-dihydro-2H-pyridin-1-ylmethyl]-8-methoxy-3,4-dihydro-2H-benzo[1,4]oxazine-4-carboxylic acid tert-butyl ester A mixture of Intermediate 6 (1.3 g, 2.9 mmol) and 5-fluoro-3-(1,2,3,6-tetrahydro-4-pyridinyl)-1H-indole (0.9 g, 4.5 mmol) in anhydrous dimethyl sulfoxide (15 ml) was heated to 80° C. for 2 hours. The mixture was poured into water (basic solution) and extracted with ethyl acetate and washed with water and brine. The organic layer was dried over anhydrous magnesium sulfate, filtered and concentrated to give 1.0 g of product. Chromatographed (100% ethyl acetate) afforded 0.8 g (57.2%) of product as a yellow foam.

INTERMEDIATE 8

(8-Methoxy-4-methyl-3,4-dihydro-2H-benzo[1,4]oxazin-2-yl)-methanol

A mixture of Intermediate 4 (1.5 g, 7.7 mmole), anhydrous potassium carbonate (2.2 g.,1.59 mmole) and methyl iodide in N,N-dimethylformamide (60 ml.) were stirred at room temperature for 6 hours. The reaction mixture was poured in water and extracted with ethyl acetate (3×100 ml). The combined organic layers were washed with water (100 ml) and with brine (100 ml). The solution was dried over anhydrous magnesium sulfate, filtered and concentrated to give 1.7 g crude product which was chromatographed (ethyl acetate) to give 1.0 g (63.0% yield) of product as a thick oil: $^1$H NMR (400 MHz, DMSO-$d_6$): δ 2.79 (3H, s), 3.00 (1H, m), 3.25 (1H, m), 3.48–3.66 (2H, m), 3.68 (3H, s), 4.07 (1H, m), 4.92 (1H, m) 6.36 (2H, dd, J=1.32, 8.66 Hz), 6.69 (1H, t, J=8.13Hz); MS m/e 209 (M+).

Elemental analysis for $C_{11}H_{15}NO_3$

Calc'd: C, 63.14; H, 7.23; N, 6.69

Found: C, 61.02; H, 7.32; N, 6.44

INTERMEDIATE 9

(8-Methoxy-4-ethyl-3,4-dihydro-2H-benzo[1,4]oxazin-2-yl)-methanol

A mixture of Intermediate 4 (1.2 g, 6.1 mmole), N,N-diisopropylethylamine (0.7 g, 6.1 mmole) and iodoethane (1.4 g, 6.1 mmole) was heated at 65° for 24 hours. The reaction mixture was poured into water (100 ml) and extracted with ethyl acetate (3×100 ml). The combined organic layers were washed with water (2×100 ml), brine (100 ml), dried over anhydrous magnesium sulfate, filtered and concentrated to give 1.3 g crude product. Chromatography (ethyl acetate) gave 0.9 g (69%) of product as a solid: mp 75–77° C.; 1H NMR (400 MHz, DMSO-$d_6$): δ 1.01 (3H, t, J=7.03Hz), 3.08 (1H, m), 3.00–3.40 (4H, m), 3.48 (1H, m), 3.00–3.40 (4H, m), 3.48 (1H, m), 3.50 (1H, m), 3.63 (4.00 1H, m), 4.90 (1H broad), 6.35 (1H, dd, J=1.13, 8.31 Hz), 6.37 (1H, dd, J=1.10, 8.31 Hz), 6.66 (1H, t, J=8.13Hz); MS m/e 378 (M+).

Elemental analysis for $C_{12}H_{17}NO_3S$

Calc'd: C, 60.46; H, 6.14; N, 3.71

Found: C, 60.63; H, 6.06; N, 3.68

INTERMEDIATE 10

(8-Methoxy-4-propyl-3,4-dihydro-2H-benzo[1,4]oxazin-2-yl)-methanol

Intermediate 10 was prepared in same manner as Intermediate 9 to give 1.4 g. pure product (82%): mp 42–44° C.; $^1$H NMR (400 MHz, DMSO-$d_6$): δ 0.85 (3H, t J=7.52 Hz), 1.50 (2H, q, J=7.52 Hz), 3.05 (2H,m), 3.17 (1H, m), 3.25 (1H, m), 3.49 (1H, m) 3.61 (1H, m), 3.65 (3H, s), 3.95 (1H, m), 4.88 (1H ,broad), 6.25 (1H, d J=8.11 Hz), 6.32 (1H, d, J=7.95 Hz), 6.63 (1H, t J=8.11 Hz) IR (KBr) 3510 cm$^{-1}$; MS m/e 238 (M+).

Elemental analysis for $C_{13}H_{19}NO_3$

Calc'd: C, 65.80; H, 8.07, N,5.90

Found: C,66.05, H, 8.34, N,5.90

INTERMEDIATE 11

Toluene-4-sulfonic acid 4-methyl-8-methoxy-3,4-dihydro-2H-benzo[1,4]oxazin-2-ylmethyl ester A mixture of Intermediate 8 (0.9 g, 0.0043 mole) and p-toluenesulfonyl chloride (1.3 g, 0.0068 mole) in pyridine (30 ml) was stirred at room temperature for eighteen hours. The reaction mixture was diluted with ethyl acetate (200 ml) and washed sequentially with 2N hydrochloric acid (2×100 ml), water (2×100 ml) and brine (100 ml). The solution was dried over anhydrous magnesium sulfate and concentrated to give 1.4 g of solid which was recrystallized (1:9 ethyl acetate/hexane) to give 1.1 g (73.0%) of product: mp 124–126° C.; $^1$H NMR (400 MHz, DMSO-$d_6$): δ 2.40 (3H, s), 2.73 (3H, s), 3.00 (1H, m), 3.17 (1H, m), 3.68 (3H, s), 4.13 (1H, m), 4.22 (1H, m), 4.37 (1H, m), 6.35 (2H, dd J=1.32, 8.35 Hz), 6.68 (1H, t, J=8.13 Hz), 7.46 (2H, dd, J=0.72, 8.57 Hz), 7.79 (2H, dd, J=0.72, 8.35 Hz); MS m/e 364 (M+H+).

Elemental analysis for $C_{18}H_{21}NO_3S$

Calc'd: C, 59.49; H, 5.83; N, 3.85

Found: C, 58.70; H, 5.77; N, 3.76

INTERMEDIATE 12

Toluene-4-sulfonic acid 4-ethyl-8-methoxy-3,4-dihydro-2H-benzo[1,4]oxazin-2-ylmethyl ester Intermediate 12 was prepared in the same manner as Intermediate 11 using iodoethane to give 1.0 g of pure product in 62.5% yield: mp 90–91° C.; $^1$H NMR (400 MHz DMSO-$d_6$): δ 0.96 (3H, t, J=7.02 Hz), 2.49 (3H, s), 3.00–3.31 (4H, m), 3.68 (3H, s), 4.10–4.30 (3H, m), 6.29–6.35 (2H, d, J=9.88 Hz), 6.67 (1H, t, J=8.35 Hz), 7.46 (2H, d, J=8.13 Hz), 7.81 (2H, d, J=8.35 Hz); MS m/e 378 (M+).

Elemental analysis for $C_{19}H_{23}NO_3S$

Calc'd: C, 60.46; H, 6.14; N, 3.71

Found: C, 60.63; H, 6.06; N, 3.68

INTERMEDIATE 13

Toluene-4-sulfonic acid 4-propyl-8-methoxy-3,4-dihydro-2H-benzo[1,4]oxazin-2-ylmethyl ester Intermediate 13 was prepared in same manner as Intermediate 11 using iodopropane to give 1.5 g product (71.4%); mp 94–95° C.; $^1$H NMR (400 MHz DMSO-$d_6$): δ 0.83 (3H, t J=7.37), 1.44 (2H, q J=7.25Hz), 2.40 (3H,s), 3.00–3.22 (6H, m), 3.34 (1H, s broad), 3.67 (3H, s), 4.11 (1H, m), 4.25 (1H, m), 6.28 (1H, dd, J=8.1, 1.21 Hz), 6.33 (1H, dd J=8.35, 1.12Hz), 6.66 (1H, t, J =8.13 Hz), 7.46 (2H, d, J=7.90 Hz), 7.81 (2H, d, J=8.35 Hz); MS m/e 392 (M+).

Elemental analysis for $C_{20}H_{25}N\ O_5S$

Calc'd: C, 61.36 H, 6.44 N, 3.58

Found: C, 61.33 H, 6.41 N, 3.55

INTERMEDIATE 14

3,4-Dihydro-2H-benzo[1,4]oxazin-2-yl)-methanol

To a solution of ethyl 2,3-dihydro-benzo[1,4]oxazine-2-carboxylate ester (11.9 g, 19.0 mmol) in anhydrous tetrahydrofuran (60 mL) was added a 2M solution of lithium borohydride (15 mL) at room temperature. The reaction was allowed to proceed for 1 hour and was then quenched by the slow addition of methanol. After 2 hours, water was slowly added (100 mL) and the reaction mixture was extracted with ethyl acetate (4×100 mL). The organic layer was separated and dried over anhydrous magnesium sulfate, filtered, and the solvent removed under vacuum. Purification by chromatography (ethyl acetate-hexane-methanol-3:6: 1) to afford 1.96 g (62%) of an oil: MS (EI) m/e 165 (M+).

INTERMEDIATE 15

2-Hydroxymethyl-2,3-dihydro-benzo[1,4]oxazine-4-carboxylic acid tert-butyl ester To a solution of 3,4-dihydro-2H-benzo[1,4]oxazin-2-yl)-methanol (10.7 g, 65.0 mmol) prepared above in anhydrous tetrahydrofuran (200 mL) was slowly added di-tert-butyl dicarbonate (62 g) in tetrahydrofuran (40 mL). The reaction was heated to reflux for 4 hours and allowed to cool to room temperature and then poured into water (100 mL) and extracted with ethyl ether (3×100 mL). The organic layer was washed with water (2×50 mL) and dried over anhydrous sodium sulfate, filtered, and the solvent removed under vacuum. Chromatography (ethyl acetate-hexanes: 1:2) afforded 12.9 g of white solid (75%): mp 93.5–94.5° C.; MS (EI) 265 (M+).

Elemental analysis calculated for $C_{14}H_{19}NO_4$
Calc'd: C, 63.38: H, 7.22: N, 5.28
Found: C, 63.53: H, 7.32: N, 5.38

INTERMEDIATE 16 t-Butyl-2,3-dihydro-benzo[1,4]oxazine-4-carboxylate-2-methyltosylate

A solution of 2-hydroxymethyl-2,3-dihydro-benzo 1,4] oxazine-4-carboxylic acid tert-butyl ester (2.8 g, 10.6 mmol) and p-toluenesulfonyl chloride (3.4 g, ) in anhydrous pyridine (45 mL) was allowed to stir overnight at room temperature. The reaction mixture was quenched with 1N sodium hydroxide (50 mL) and extracted with methylene chloride (5×50 mL). The organic layer was washed with water (3×50 mL) and dried over anhydrous sodium sulfate, filtered and the solvent removed under vacuum. Chromatography (ethyl acetate-hexane, 1–3) afforded a thick oil: MS (FAB) m/e 419 (M+Na).

Elemental analysis calculated for $C_{21}H_{25}NO_6S$
Calc'd: C, 60.13: H, 6.01: N, 3.34
Found: C, 60.13: H, 6.11: N, 3.56

INTERMEDIATE 17

2-[4-(1H-indol-3-yl)-3,6-dihydro-2H-pyridin-1-ylmethyl]-3,4-dihydro-2H-benzo[1,4]oxazine-4-carboxylic acid tert-butyl ester The title compound was prepared in 29% yield by reacting Intermediate 16 with 3-(1,2,3,6-tetrahydro-4-pyridinyl-1H-indole according to the same procedure used to prepare Intermediate 7.

INTERMEDIATE 18

Ethyl 4-phenyl-2,3-dihydro-benzo[1,4]oxazine-2-carboxylate ester

A solution of ethyl 2,3-dihydro-benzo[1,4]oxazine-2-carboxylate ester (10 g, 48 mmol), 1,4-cyclohexanedione (10.8 g, 97 mmol) and p-toluenesulfonic acid (2 g) in toluene (200 mL) was heated to reflux for 4 hours. The solvent was evaporated and the product was purified by chromatography (ethyl acetate-hexane: 1–3) to afford 7.2 g (53%) of product as a yellow oil: MS (EI) m/e 283 (M+).

INTERMEDIATE 19

(4-Phenyl-3,4-dihydro-2H-benzo[1,4]oxazin-2-yl)-methanol

To a solution of ethyl 4-phenyl-2,3-dihydro-benzo[1,4] oxazine-2-carboxylate ester (6.9 g, (24 mmol) in anhydrous tetrahydrofuran (80 mL) was added 60 mL of 2M lithium borohydride in tetrahydrofuran (0.12 mmol) at room temperature. The reaction mixture was stirred at room temperature for 4 hours and quenched with methanol. The reaction was poured into water (100 mL) and extracted with ether (3×80 mL) and the combined organic layers dried over anhydrous sodium sulfate, filtered, and the solvent removed under vacuum. Chromatography (ethyl aceate-hexanes; 1–3) afforded 5.7 g (96%) of product as a clear oil: MS (El) m/e 213 (M⁺).

Elemental analysis calculated for $C_{15}H_{15}NO_2$
Calc'd: C, 74.67: H, 6.27: N, 5.81
Found: C, 74.21: H, 6.60: N, 5.56

INTERMEDIATE 20

Toluene sulfonic acid 4-phenyl-3,4-dihydro-2H-benzof1,4]oxazin-2-yl-methyl ester (4-Phenyl-3,4-dihydro-2H-benzo[1,4]oxazin-2-yl)-methanol (5.6 g, 23 mmol) was reacted according to the procedure as described above for Intermediate 11 to afford 8.2 g (89%) of the title compound: mp 83–85° C.

Elemental analysis calculated for $C_{21}H_{21}NO_4S$
Calc'd: C, 66.82: H, 5.35: N, 3.80
Found: C, 66.53: H, 5.39: N, 3.40

INTERMEDIATE 21

3-(1,2,3,6-Tetrahydro-pyridin4-yl)-1H-pyrrolo[2,3-b]pyridine

7-Azaindole (10 g, 85 mmol), 4piperidone (34 g,0.22 mol) and potassium hydroxide (16.83 g, 0.3 mol) were heated to reflux in 150 ml methanol overnight. The reaction was cooled, filtered and concentrated to give an orange slurry. The slurry was then extracted with methylene chloride and washed with water. The organic layer was dried over anhydrous magnesium, filtered and concentrated to afford 14.2 g (84%) of product as a solid: mp 195–199° C.

INTERMEDIATE 22

[8-Methoxy-4-(4-trifluoromethyl-phenyl)-3,4-dibydro-2H-benzo[1,4]oxazin-2-yl]-methanol Intermediate 4 (0.62 g, 3.2 mmol), 4-iodobenzotrifluoride (2.25 g, 8.32 mmol), powdered anhydrous potassium carbonate (1.76 g, 12.8 mmol), electrolytic oopper powder (0.81 g, 12.8 mmol) and 18-crown-6 (0.23 g, 0.64 mmol) were refluxed in o-dichlorobenzene (50 mL) for 4 hours under nitrogen. The inorganic salts were removed by filtration of the hot reaction mixture. The solvent was distilled under reduced pressure and the residue was chromatographed (30% ethyl acetate-hexanes) to afford 0.43 g (40%) of product as an oil: $^1$H NMR (400 MHz, CDCl$_3$) δ 2.10

(2H, bs, OH), 3.69 (1H, m), 3.83 (1H, m), 3.89 (3H, s), 3.91 (2H, m), 4.60 (1H, m), 6.53 (1H, dd, J=8.3, 1.4 Hz), 6.71 (1H, dd, J=8.3, 1.4 Hz), 6.73 (1H, t, J=8.3 Hz), 7.26 (2H, d, J=8.79 Hz), 7.54 (2H, d, J=8.79 Hz); IR (film) 3080, 2900, 1600, 1475, 1375 cm-1; MS m/e 494 ((M+H+).

Elemental analysis calculated for $C_{17}H_{16}FNO_3$

Calc'd: C, 60.18: H, 4.75: N, 4.13

Found: C, 60.18: H, 4.61: N, 4.37

INTERMEDIATE 23

Toluene-4-sulfonic acid, [8-Metboxy-4-(4-trifluoromethyl-phenyl)-3,4-dihydro-2H-benzo[1,4]oxazin-2yl]-methyl ester Intermediate 23 was prepared from Intermediate 22 in the maimer as described for Intermediate 16 to give 0.41 g (92%) of the title compound as an oil: $^1$H NMR (400 MHz, CDCl$_3$) δ 2.42 (3H,s), 3.63 (2H, m), 3.82 (2 H, m), 3.88 (3H, s), 4.10 (1H, m), 4.41 (1H, m), 4.50 (1H, m), 6.50 (1H, dd, J=8.1, 1.5 Hz), 6.64 (1H, dd, J=8.1, 1.5 Hz), 6.72 (1H, t, J=8.1 Hz), 7.20 (2H, d, J=8.5Hz), 7.27 (2H, d, J=8.1 Hz), 7.54 (2H, d, J=8.5 Hz), 7.68 (2H, d, J=8.1 Hz); IR (film) 3080, 2900, 1600, 1475, 1325 cm-1; MS m/e 494 (M+H+).

Elemental analysis calculated for $C_{24}H_{22}F_3NO_5S.0.1 CH_2Cl_2$

Calc'd: C, 57.66: H, 4.46: N, 2.79

Found: C, 57.55: H, 4.30: N, 2.82

EXAMPLE 1

2-[4-(5-Fluoro-1H-indol-3-yl)-3,6-dihydro-2H-pyridin-1-ylmethyl]-8-methoxy-3,4-dihydro-2H-benzo[1,4]oxazine A mixture of Intermediate 7 (0.8 g, 1.6 mmol) in methylene chloride (15 ml) and trifluoroacetic acid (1.5 ml) was stirred at room temperature for 6 hours. The reaction mixture was poured in 10% sodium bicarbonate and extracted with ethyl acetate. The combined organic layers were washed with water and brine, then dried over anhydrous magnesium sulfate. Filtration and concentration under vacuum followed by chromatography (5% ammonia in methanol-ethyl acetate) afforded 0.3 g (67%) of product as a yellow solid: mp° C. The oxalate salt was prepared in ethanol: mp 162–166° C.

Elemental analysis for $C_{23}H_{24}FN_3O_2.0.8C_2H_2O_4$

Calc'd: C, 63.48; H, 5.54; N, 9.03

Found: C, 63.22; H, 5.70; N, 8.87

EXAMPLE 2

2-[4-(5-Fluoro-1H-indol-3-yl)-3,6-dihydro-2H-pyridin-1-ylmethyl]-8-methoxy-4-methyl-3,4-dihydro-2H-benzo[1,4]oxazine A mixture of Intermediate 11 (4 g, 0.0011 mole), 5-fluoro-3-(1,2,3,6-tetrahydro-4-pyridinyl-1H-indole (0.7 g 0032 mole) and dimethylsulfoxide (15 ml) was heated to 80° for 2 hours. The reaction mixture was poured into water (100 ml) and extracted with ethyl acetate (3×100 ml). The combined organic layers were washed with water (100 ml) and brine (100 ml), dried over anhydrous magnesium sulfate, filtered and concentrated to give 0.35 crude product. Chromatography (3% methanol-ethyl acetate) gave 0.8 g (60%) of product. The oxalate salt was prepared: mp 218–219° C.; $^1$H NMR (400 MHz, DMSO-d$_6$): δ 2.73 (2H, s broad), 2.82 (3H, s), 3.;09–3.31 (4H, m), 3.43 (1H, m), 3.73 (3H, s), 3.76–3.81 (2H, m), 4.64 (1H, s broad), 6.09 (1H, s, broad), 6.42 (1H, dd, J=2.85, -8.12 Hz), 6.75 (1H, t, J=8.13 Hz), 6.97 (1H, dt, J=2.42, 9.00 Hz), 7.40 (1H, d, J 8.79 Hz), 7.71 (1H, m), 11.38 (1H, bs); IR (KBr) 3300 cm-1; MS m/e 408 (M+).

Elemental analysis for $C_{24}H_{26}F_3O_2.C_2H_2O_4$

Calc'd: C, 62.;73; H, 5.67; N, 3.85

Found: C, 62.33; H, 5.77; N, 3.76

EXAMPLE 3

2-[4-(5-Fluoro-1H-indol-3-yl)-3,6-dibydro-2H-pyridin-1-ylmetbyl]-8-methoxy-4-ethyl-3,4-dihydro-2H-benzo[1,4]oxazine The title compounds was prepared by treating Intermediate 12 with 5-fluoro-3-(1,2,3,6-tetrahydro-4pyridinyl)-1H-indole in the same manner as Example 2 to give 9.35 g of product (63%) which was converted to oxalate salt: mp 197–199° C.; $^1$H NMR (400 MHz, DMSO-d$_6$): δ 1.06 (3H, t, J=6.81), 2.72 (2H, s broad), 3.10–3.41 (9H, m), 3.74 (3H, s), 4.54 (1H, s broad), 6.11 (1H, s), 6.36 (1H, d, J=8.35 Hz), 6.43 (1H, J=8.35 Hz), 6.74 (1H, s), 7.00 (1H, dt, J=2.74, 9.00), 7.41 (1H, m), 7.61 (2H, m),11.35 (1H, s broad); IR (KBr) 3400, 3300 cm-1; MS m/e 422 (M+).

Elemental analysis for $C_{25}H_{28}FN_3O_2$

Calc'd: C, 63.36; H, 5.91; N, 8.21

Found: C, 63.48; H, 5.86; N, 8.32

EXAMPLE 4

2-[4-(5-Fluoro-1H-indol-3-yl)-3,6-dihydro-2H-pyridin-1-ylmethyl]-8-methoxy-4-propyl-3,4-dihydro-2H-benzo[1,4]oxazine The title compound was prepared by treating Intermediate 13 with 5-fluoro-3-(1,2,3,6-tetrahydro-4-pyridinyl-1H-indole in same manner as Example 2 to give 0.3 g (60%) of product which was converted to oxalate salt: mp 209–211° C.; $^1$ H NMR (400 MHz DMSO-d$_6$): δ 0.88 (3H, t J=7.25Hz), 1.53 (2H, q, J=7.47), 3.11–3.38 (10 H, m), 3.73 (3H, s) 3.75 (1H,m), 4.52 (1H, m), 6.06 (1H, s), 6.41 (2H, dd J=8.11, 0.6Hz) 6.71 (1H, t ), 6.99 (1H dt, J=9.00, 2.42Hz), 7.39 (1H, m), 7.57 (2H, m); IR (KBr) 3300 cm-1; MS m/e 436 (M+).

Elemental analysis for $C_{26}H_{30}F N_3O_2$

Calc'd: C, 63.95 H, 6.13 N,7.99

Found: C, 64.24 H, 6.19 N, 7.98

EXAMPLE 5

2-[4-(1H-Indol-3-yl)-3,6-dihydro-2H-pyridin-1-ylmethyl]-3,4-dihydro-2H-benzo[1,4]oxazine The title compound was prepared according to the procedure used for Example 1 using Intermediate 17 (31%). The oxalate salt was prepared to afford an orange solid: mp 135–140° C.

Elemental analysis for $C_{22}H_{23}N_3O.C_2H_2O_4$

Calc'd: C, 66.15 H, 5.78 N,9.64

Found: C, 67.21 H, 5.84 N, 9.76

EXAMPLE 6

4-Phenyl-2-[4-(1H-pyrrolo[2,3,b]pyridin-3yl)-3,6-dihydro-2H-pyridin-1-ylmethyl]-3,4-dihydro-2H-benzo[1,4]oxazine The title compound was prepared by reacting Intermediates 20 and 21 according to the same procedure used to prepare Intermediate 17 to afford 0.35 g (75%) of product as a white solid: mp 187–188 C.; $^1$H NMR (400 MHz), DMSO-d$_6$) δ 2.44 (2H, s), 2.66 (3H, m), 2.75 (1H, m), 3.18 (2H, m), 3.55 (1H, dd, J=7.0, 12.5 Hz), 3.76 (1H, dd, J=2.5, 12.5 Hz), 4.41 (1H, m), 6.10 (1H, s), 6.65 (2H, m), 6.82 (2H, m), 7.03 (2H, m), 7.22 (2H, d, J=7.5 Hz), 7.35 (2H, J=7.5 Hz), 7.46 (1H, d, J=2.4 Hz), 8.18 (2H, m) 11.60 (1H, s): IR (3400, 3080, 2900, 2850, 1700, 1500, 1280, 1250 cm$^{-1}$; MS m/e 423 (M+H+).

EXAMPLE 7

2-[4-(5-Fluoro-1H-Indol-3-yl)-3,6-dihydro-2H-pyridin-1-ylmethyl]-8-methoxy-4-(4-trifluoromethyl-phenyl)-3,4-dihydro-2H-benzo[1,4] oxazine The title compound was prepared by treating 5-fluoro-3-(1,2,3,6-tetrahydro4-pyridinyl)-1H-indole with Intermediate 23 according to the same procedure used to prepare Intermediate 17 to afford 0.12 g (68%) of product as a solid: mp 181–182° C.,: $^1$H NMR (400 MHz), DMSO-δ6) δ 2.65 (2H, m), 3.18 (3H, m), 3.30 (1H, m), 3.61 (2H, m), 3.75 (1H, m), 3.80 (3H, s), 3.90 (1H, d, J=9 Hz), 4.61 (1H, m), 6.06 (1H, s), 6.63 (1H, d, J=8.1 Hz), 6.69 (1H, d, J=8.1 Hz), 6.76 (1H, t, J=8.1 Hz), 6.96 (1H, dt, J=2.85, 9.0 Hz), 7.36 (1H, m), 7.38 (2H, d, J=8.78 Hz), 7.53 (1H, s), 7.55 (1H, m), 7.65 (2H, d, J=8.78 Hz), 11.35 (1H, bs): IR (KBr) 3450, 3080, 2900, 2600, 1750, 1600, 1475, 1325 cm$^{-1}$; MS m/e 538 (M+H+).

The activity of the present compounds is demonstrated by the following standard pharmacological test procedures.

The PCR cloning of the human $^5$-HT$_{1A}$ receptor subtype from a human genomic library has been described previously by Chanda et al., Mol. Pharmacol., 43:516 (1993). A stable Chinese hamster ovary cell line expressing the human S-HT$_{1A}$ receptor subtype (5-HT$_{1A}$.CHO cells) was employed throughout this study. Cells were maintained in DMEM supplemented with 10% fetal calf serum, non-essential amino acids and penicillin/ streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at –80.C. On the day of assay, the cells were thawed on ice, and resuspended in buffer. Studies were conducted using [$^3$H]8-OH-DPAT as the radioligand. The binding assay was performed in 96 well mnicrotiter plates in a final total volume of 250 μL of buffer. Comparison experiments were performed by using 7 concentrations of unlabelled drug and a final ligand concentration of 1.5 nM . Non-specific binding was determined in the presence of 10 μM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester Gaithersburg, Md.) through a GF/B filter pre-soaked for 30 minutes in 0.5% polyethyleneimine.

A protocol similar to that used by Cheetham et al., Neuropharmacol. , 32:737 (1993) was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 μM) to define specific binding. All reactions were terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method of Cheng and Prusoff, Biochem. Pharmacol., 22:3099 (1973); Ki=IC50/((Radioligand conc.)/(1+KD)).

The [$^{35}$S]-GTPγS binding assay was similar to that used by Lazareno and Birdsall, Br. J. Pharmacol. 109:1120 (1993). Briefly, 5-HT$_{1A}$ cloned receptor membrane fragments (as used for 5-H$_{1A}$ receptor binding assays) were stored at −70° C. until needed. When needed, membranes were rapidly thawed, centrifuged at 40,000×g for 10 minutes and resuspended at 4° C. for 10 minutes in assay buffer (25 mM HEPES, 3 mM MgCl$_2$, 100 mnM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions are terminated by the addition of ice cold Tris buffer followed by rapid filtration using a Tom Tech® filtration device to separate bound from free [$^{35}$S]GTPgS. Agonists produce an increase in the amount of [$^{35}$S]GTPgS bound whereas antagonists produce no increase in binding. Bound radioactivity was counted and analyzed as above.

The following assays were performed by incubating the cells with DMEM containing 25 mM HEPES, 5 mM theophylline and 10 μM pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at −20° C. prior to assessment of cAMP formation by a cAMP SPA assay (Amersham).

| Example | 5-HT$_{1A}$ (Ki, nM, % Inh. @ .1 μM) | ST (K$_i$, nM) | GTPγS Emax (%) |
|---|---|---|---|
| 1 | 155 | 3.7 | 10 |
| 2 | 140 | 8.5 | 97 |
| 3 | 137 | 12.0 | 62 |
| 4 | 363 | 20.0 | 100 |
| 5 | 805 | 0.74 | 57 |
| 6 | 20% | 106 | 0 |
| 7 | 0% | 505 | — |

Such compounds are therefore potentially useful for the treatment of depression as well as other serotonin disorders.

The compounds of the present invention may be administered orally or parentally, neat or in combination with conventional pharmaceutical carriers. Applicable solid carriers for pharmaceutical compositions containing the compounds of this invention can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula:

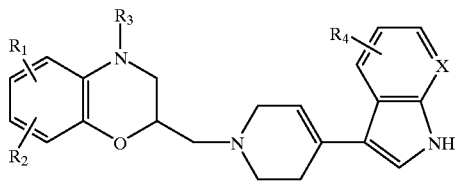

wherein:

$R_1$ is hydrogen or halogen;

$R_2$ is hydrogen, alkoxy or carboximide;

$R_3$ is hydrogen, alkyl, alkylaryl, alyl or substituted aryl;

$R_4$ is hydrogen, CN, halogen or carboximide; and

X is CH or N; or pharmaceutically acceptable salts thereof.

2. A compound as in claim 1, wherein:

$R_1$ is hydrogen;

$R_2$ is alkoxy or hydrogen;

$R_3$ is hydrogen, alkyl or alkylaryl;

$R_4$ is halogen or hydrogen; and

X is CH or N; or pharmaceutically acceptable salts thereof.

3. The compound of claim 1 which is 2-[4(5-Fluoro-1H-indol-3-yl)-3,6-dihydro-2H-pyridin-1-ylmethyl]-8-methoxy-3,4-dihydro-2H-benzo[1,4]oxazine.

4. The compound of claim 1 which is 2-[4-(5-Fluoro-1H-indol-3-yl)-3,6-dihydro-2H-pyridin-1-ylmethyl]-8-methoxy-4-methyl-3,4-dihydro-2H-benzo[1,4]oxazine.

5. The compound of claim 1 which is 2-[4-(5-Fluoro-1H-indol-3-yl)-3,6-dihydro-2H-pyridin-1-ylmethyl]-8-methoxy-4-ethyl-3,4-dihydro-2H-benzo[1,4]oxazine.

6. The compound of claim 1 which is 2-[4-(5-Fluoro-1H-indol-3-yl)-3,6-dihydro-2H-pyridin-1-ylmethyl]-8-methoxy-4-propyl-3,4-dihydro-2H-benzo[1,4]oxazine.

7. The compound of claim 1 which is 2-[4(1H-Indol-3-yl)-3,6-dihydro-2H-pyridin-1-ylmethyl]-3,4-dihydro-2H-benzo[1,4]oxazine.

8. The compound of claim 1 which is 4-Phenyl-2-[4-(1H-pyrrolo[2,3,6]pyridin-3-yl)-3,6-dihydro-2H-pyridin-1-ylmethyl]-3,4-dihydro-2H-benzo[1,4]oxazine.

9. The compound of claim 1 which is 2-[4-(5-Fluoro-1H-indol-3-yl)-3,6-dihydro-2H-pyridin-1-ylmethyl]-8-methoxy-4-(4-trifluoromethyl-phenyl)-3,4-dihydro-2H-benzo[1,4]oxazine.

10. A pharmaceutical composition comprising a compound of the formula:

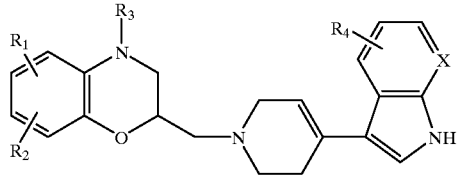

wherein:

$R_1$ is hydrogen or halogen;

$R_2$ is hydrogen, alkoxy or carboximide;

$R_3$ is hydrogen, alkyl, alkylaryl, aryl or substituted aryl;

$R_4$ is hydrogen, CN, halogen, or carboximide; and

X is CH or N; or pharmaceutically acceptable salts thereof.

11. A method for treating depression in a patient in need thereof, comprising administering to said patient an antidepressant effective amount of a compound of the formula:

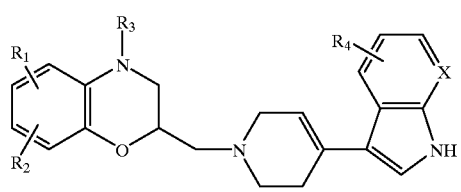
wherein:
R₁ is hydrogen or halogen;
R₂ is hydrogen, alkoxy or carboximide;
R₃ is hydrogen, alkyl, alkylaryl, aryl or substituted aryl;
R₄ is hydrogen, CN, halogen, or carboximide; and
X is CH or N; or pharmaceutically acceptable salts thereof.
* * * * *